(12) United States Patent
Heinz et al.

(10) Patent No.: US 6,213,968 B1
(45) Date of Patent: Apr. 10, 2001

(54) CUSTOM FITTED ORTHOTIC DEVICE

(75) Inventors: Thomas J. Heinz, Flintridge; Dae Shik Park, Fullerton, both of CA (US)

(73) Assignee: BioCybernetics International, Irvine, CA (US)

( * ) Notice: Subject to any disclaimer, the term of this patent is extended or adjusted under 35 U.S.C. 154(b) by 0 days.

(21) Appl. No.: 09/334,649

(22) Filed: Jun. 17, 1999

Related U.S. Application Data

(60) Provisional application No. 60/089,707, filed on Jun. 18, 1998.

(51) Int. Cl.[7] ........................................ A61F 5/00
(52) U.S. Cl. .............................................. 602/19
(58) Field of Search .............................. 602/19; 128/96.1, 128/100.1, 101.1, 102.1; 2/312

(56) References Cited

U.S. PATENT DOCUMENTS

| Re. 35,940 | 10/1998 | Heinz et al. . |
| 2,554,337 | 5/1951 | Lampert . |
| 4,508,110 | 4/1985 | Modglin . |
| 5,599,287 | 2/1997 | Beczak, Sr. et al. . |
| 5,634,891 | 6/1997 | Beczak, Sr. et al. . |

*Primary Examiner*—Kim M. Lewis
(74) *Attorney, Agent, or Firm*—Arent Fox Kintner Plotkin & Kahn

(57) ABSTRACT

An orthotic device is provided, including an orthosis body adapted to be wrapped around the torso of a wearer of the device, the orthosis body having at least two segments in juxtaposed relationship. Means are provided at free end portions of the at least two segments to releasably secure the free end portions to one another. At least two cables are provided, each cable operatively connected to the at least two segments. At least two sets of pulleys are mounted on the at least two segments with each cable operatively connected to the at least two segments running through a pulley on each of the at least two segments in alteration, shortening of each cable pulling the at least two segments together and tightening the orthotic device with the aid of a mechanical advantage dependent upon the number of pulleys mounted on each of the at least two segments.

42 Claims, 11 Drawing Sheets

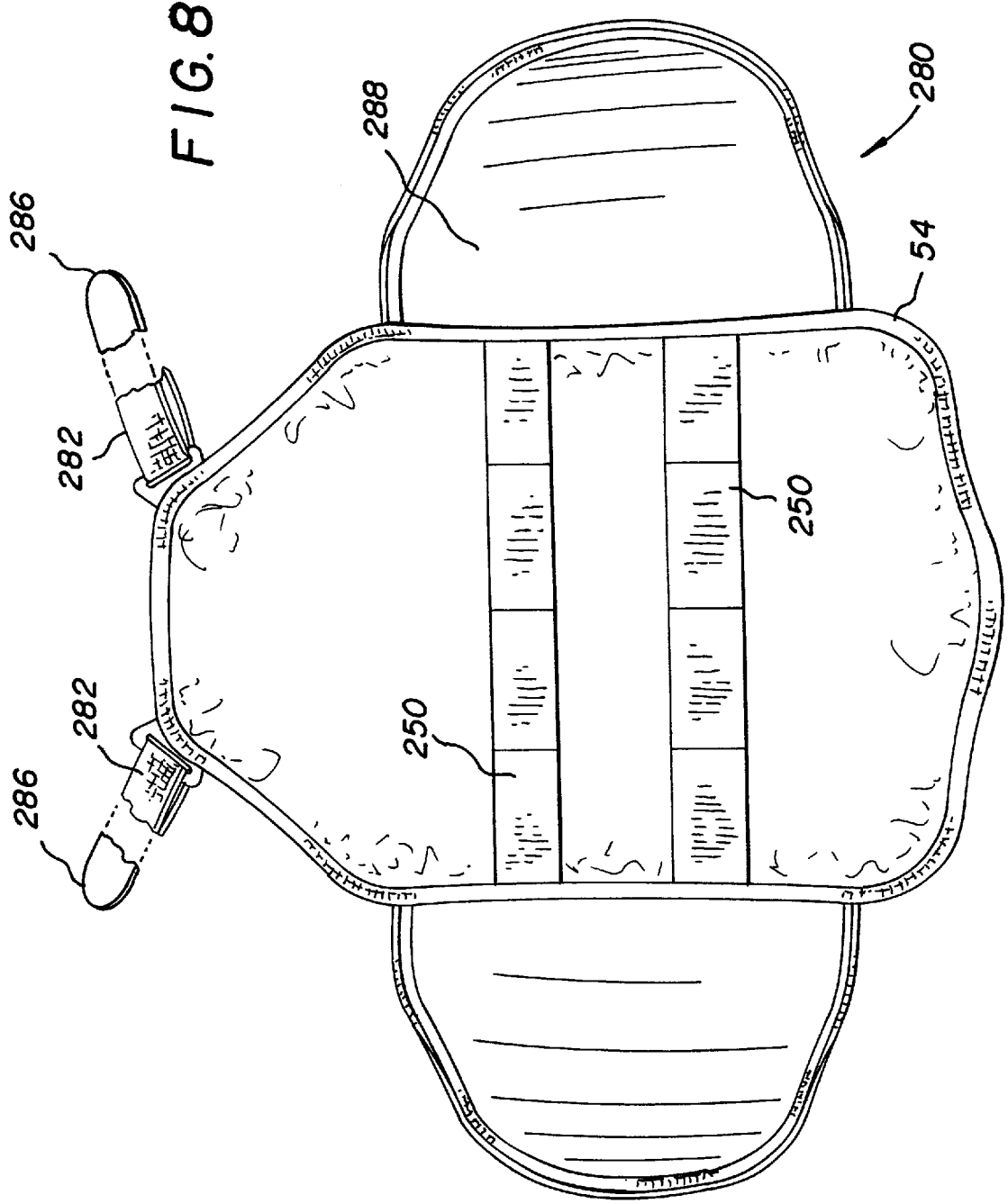

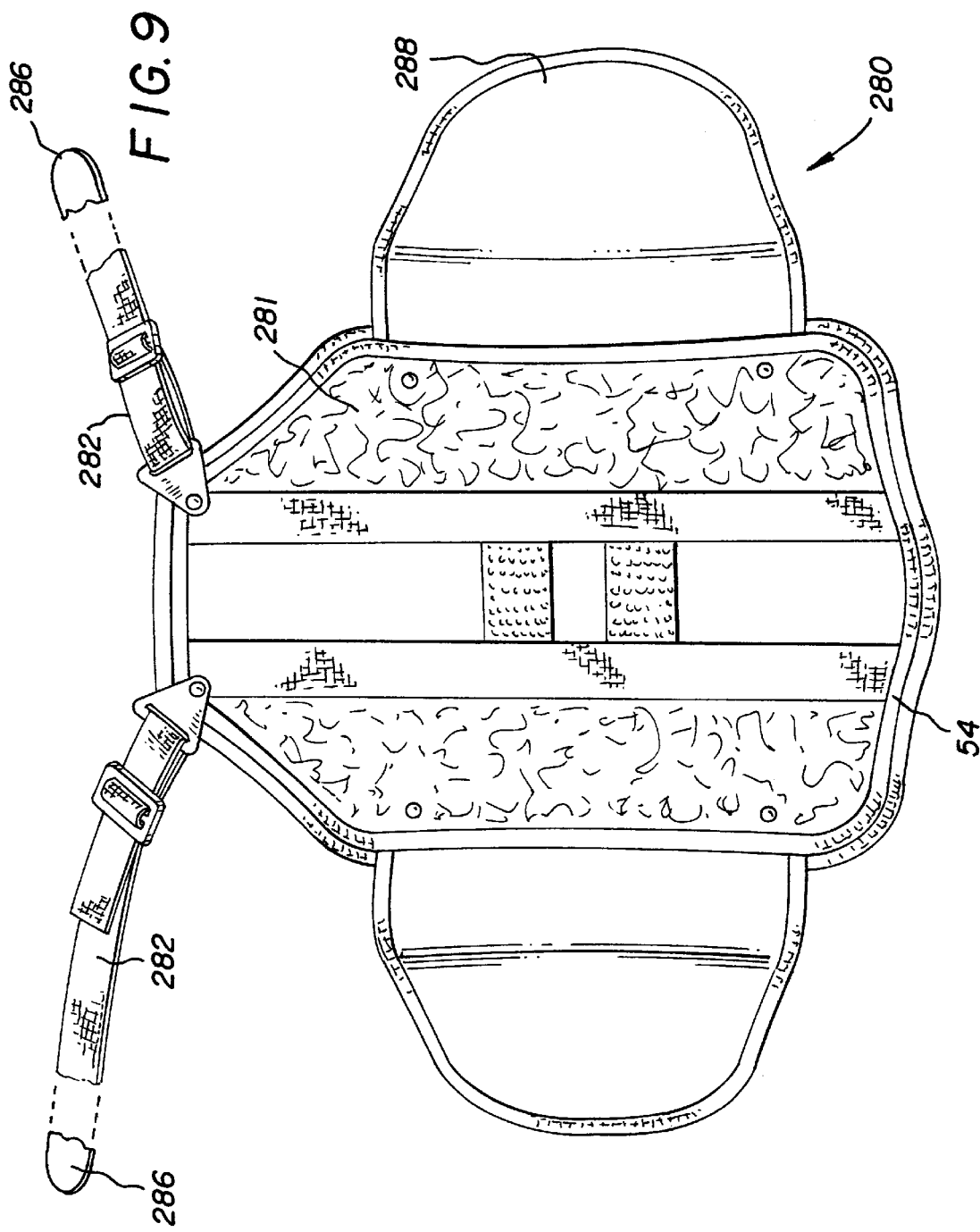

CUSTOM FITTED ORTHOTIC DEVICE

This application claims the benefit of provisional No. 60/089,707 filed Jun. 18, 1998.

TECHNICAL FIELD

The invention relates to body braces and other orthotic devices used in the treatment of spinal disorders and/or used subsequent to surgery where flexing of the torso is to be minimized. More particularly, the invention relates to back brace apparatus and orthotic devices for partial or substantial immobilization of portions of the torso, the devices having multiple modes of adjustment facilitating both rapid donning and doffing and individualized adjustment to fit the user of the device.

BACKGROUND ART

A common method of alleviating pain in people suffering from back injuries and promoting healing in post-operative back surgery patients is to stabilize the spine by means of an orthosis, such as a brace. Such braces include a multitude of materials and designs which can be snugly fitted around the patient's trunk. The back portion of such orthosis may also be provided with pockets into which are inserted lordotic pads for treating spinal lordosis.

Such braces are effective in achieving spinal stability if worn properly and consistently; however, most patients have difficulty in manually adjusting the brace to fit tightly enough to provide adequate support. This is especially true in the case of post-operative patients who are generally in pain and frequently lack sufficient strength to make the necessary adjustments. This is also true when the devices cover a large portion of the torso or when materials used in the construction of the orthoses are rigid. For many patients suffering spinal ailments, these braces are also difficult to don, appropriately position and fasten and subsequently remove. This is also particularly true when the devices are large or cumbersome or when they are constructed from rigid materials. In addition, because of the structures of many of these devices and/or the choice of materials used in their construction, the orthoses are quite uncomfortable, in many instances inducing extensive perspiring and/or chafing. Without being consistently worn and properly adjusted, such patient noncompliance obviously reduces the effectiveness of the brace.

Another frequently encountered problem with these types of braces is their inability to conform to the torso as the patient moves from a standing to a sitting position or vice versa. Thus, although such a device may have been properly adjusted initially, the patient is required to make any necessary adjustments manually to vary the tension, depending on whether the patient is standing or sitting. Similar situations and corresponding adjustments may be required as, or shortly after, a meal is consumed or digested. In addition, it is often difficult to adjust the brace to have exactly the same amount of tension that a patient previously found acceptable or even to set a particular tension for a particular patient.

Advances have been made in recent years to provide orthotic devices which can be more easily adjusted to the individual patient and readjusted when their physical position changes. Thus, in U.S. Pat. No. Re 35,940 an electromechanical back brace apparatus is described which is provided with an electromechanical mechanism for tightening the brace around the trunk of the patient to a desired tension. A cable and pulley arrangement is tightened by a small motor to provide the desired tension in the brace. A microprocessor is also provided to control the motor to obtain desired repeatable tension settings. While such a device facilitates rapid and repeatable adjustment of such a brace, the inclusion of an electromechanical mechanism and a microprocessor increases the cost of such a device to a patient or to their medical insurance program. In addition, there is the need to periodically replace batteries to power the electrically operated components.

In some situations larger orthotic devices are necessary either because the portion of the torso being supported constitutes a large volume or because the user of the device is large. In such situations, a single means for tensioning the device over a large area proves somewhat ineffective since the dimensions of the portion of the torso being supported or in which there is contact with the device vary significantly. That is, a single means of adjustment may not provide the necessary conformity to the physical profile of the patient or may provide too little tension or support to achieve the orthotic objectives with respect to a specific portion of the torso while imparting excessive tension or pressure to other parts of the torso.

Accordingly, it is an object of the present invention to provide orthotic devices which result in greater patient compliance since the key to successful orthotic treatment is patient compliance. The attributes of an effective orthotic device which induces patient compliance includes ease of donning an doffing the device, ease of adjusting the device, comfort to the wearer of the device, and effective heat dissipation. More specifically, it is a primary object of this invention to provide orthoses which may be tightened around the torso of a patient to provide the necessary support with the minimal physical effort required on the part of the patient.

It is another object of the invention to provide orthoses which are easily donned and doffed. It is a further object of the present invention to include individual controls for adjustment and custom fitting of different parts of the orthotic device. It is an additional object to provide substantially the same pressure to all portions of the torso supported by the orthosis.

It is another object of the present invention to provide multiple modes of adjustment to achieve individualized adjustment of various portions of orthosis. It is still another object of the present invention to provide multiple and independent means of adjustment of various portions of an orthotic device. It is yet another object of the present invention to provide a rigid back brace apparatus having a significant mechanical advantage that may be individually adjusted to a desired tension and conformity to an individual patient's dimensions.

It is yet another object of the present invention to provide a thoracic lumbar sacral orthosis (TLSO) which is provided with multiple means of adjustment for individually fitting to a patient.

It is another object of the invention to provide an orthotic device which is capable of being rapidly adjusted and, where appropriate, readjusted to an appropriate tension. It is another object of the present invention to provide an orthotic device to be easily disassembled to clean component parts of the device. It is also an object of the invention to provide orthoses which are comfortable and which readily dissipate body heat.

DISCLOSURE OF INVENTION

The present invention is directed to braces and orthotic devices which result in significantly increased patient compliance. This is attributable to orthoses that are both easily donned and doffed as well as being easily and rapidly adjustable to accommodate changes in the position of a wearer of the device. The orthotic devices of the invention include multiple modes of adjustment which are independently adjustable to accommodate and conform to varying physical profiles of a user of the device as well as to accommodate a change in the position of the torso about which the devices are secured. The devices of the invention provide greater patient comfort and adjustability and result, therefore, in greater patient compliance. Preferably, component parts of the devices may be easily dissembled and assembled for cleaning.

The orthotic devices of the present invention, include an orthosis or brace body adapted to be wrapped around the torso or trunk of a user, the brace body including at least two segments. Fasteners are provided at the distal or outer ends of the segments of the brace body to detachably secure the ends around a users torso. At least two cables are operatively connected to the at least two segments. The orthotic devices include at least two independent sets of pulleys, each set mounted on adjacent sides of opposing segments with each cable running through a pulley on each adjacent segment in series and in alteration, shortening of each cable pulling the adjacent segments together and tightening the brace apparatus with the aid of mechanical advantage dependent upon the number of pulleys mounted in each set of pulleys on each brace segment.

In one embodiment of the invention, the brace body includes at least two segments and employs at least two independent sets of pulleys arranged vertically with one set disposed above the other(s). In another embodiment of the invention, at least two sets of pulleys are arranged horizontally with one set disposed in opposition to the other(s). In each of these embodiments, several separate and independent means of adjustment are provided, preferably including separate adjusters for each pulley set.

In the latter embodiment of the invention, the brace body includes at least three brace body segments and at least two independent pulley sets with at least one set of pulleys securing a centrally disposed brace body segment to a first lateral segment at one side of the central brace segment and at least one other set of pulleys joining the centrally disposed brace segment to a second lateral brace segment disposed at an opposing side of the central brace segment.

To facilitate disassembly and cleaning of the devices of the invention, many of the component parts are preferably constructed to be easily detached and separated from other component parts. This includes each pulley set and its connecting cable. Thus, in a preferred embodiment, each set of pulleys comprises two modular banks of pulleys which are detachably secured to adjacent brace segments. A cable is provided to connect pulleys in the opposing banks of pulleys in a set in series and in alteration. The ends of each cable preferably may be joined to form an endless cable or are attached to a handle which also achieves the effect of an endless cable. Preferably, the handle may be removed from the body of the device when the modular banks of a pulley set are removed.

Although useful for custom fitting the orthotic device to the physical profile of an individual wearing the device, in most situations, the individualized control of adjustment and fitting of orthotic devices according to the invention is also quite effective when the device is intended to cover a large portion of the torso of the wearer or the wearer is tall. Thus, it has been found that attempting to provide both the necessary support with the appropriate tension as well as providing sufficient comfort to the wearer of a brace or other orthotic device frequently falls short when a single means of control is provided to adjust the tension of the device to suitably support and comfortably fit the affected portion of the torso, particularly when the extent of support extends over a large region of the torso in the longitudinal direction of the body of the user wearing the device or when the orthosis is constructed of rigid materials. Providing a plurality of separate adjustment devices, as in the invention, preferably at least two separate means of adjustment, allows for individualized fitting for appropriate support and comfort over the surface area covered by the device.

To improve appropriate support when used as a back brace, such as in a body jacket, an embodiment of the present invention includes a modular lordotic pad system. The system includes one or more flexible and compressible pads having a size and contour appropriate to the dimensions of the wearer of the device, preferably located in the portion of the brace corresponding to the lumbar region of the back.

BRIEF DESCRIPTION OF DRAWINGS

Other objects, features and advantages will become evident in light of the following detailed description, considered in conjunction with the referenced drawings of preferred embodiments according to the present invention. It should be understood that these drawings are exemplary only and should not be construed as limiting the invention in any way.

FIG. 8 illustrates an inner side of a rear component piece which forms part of a thoracic lumbar sacral orthosis (TLSO) used in conjunction with an embodiment of the present invention such as that illustrated in FIG. 7;

FIG. 9 is an outer side of the rear component piece of the TLSO shown in FIG. 8;

MODES FOR CARRYING OUT THE INVENTION

Figure 1:
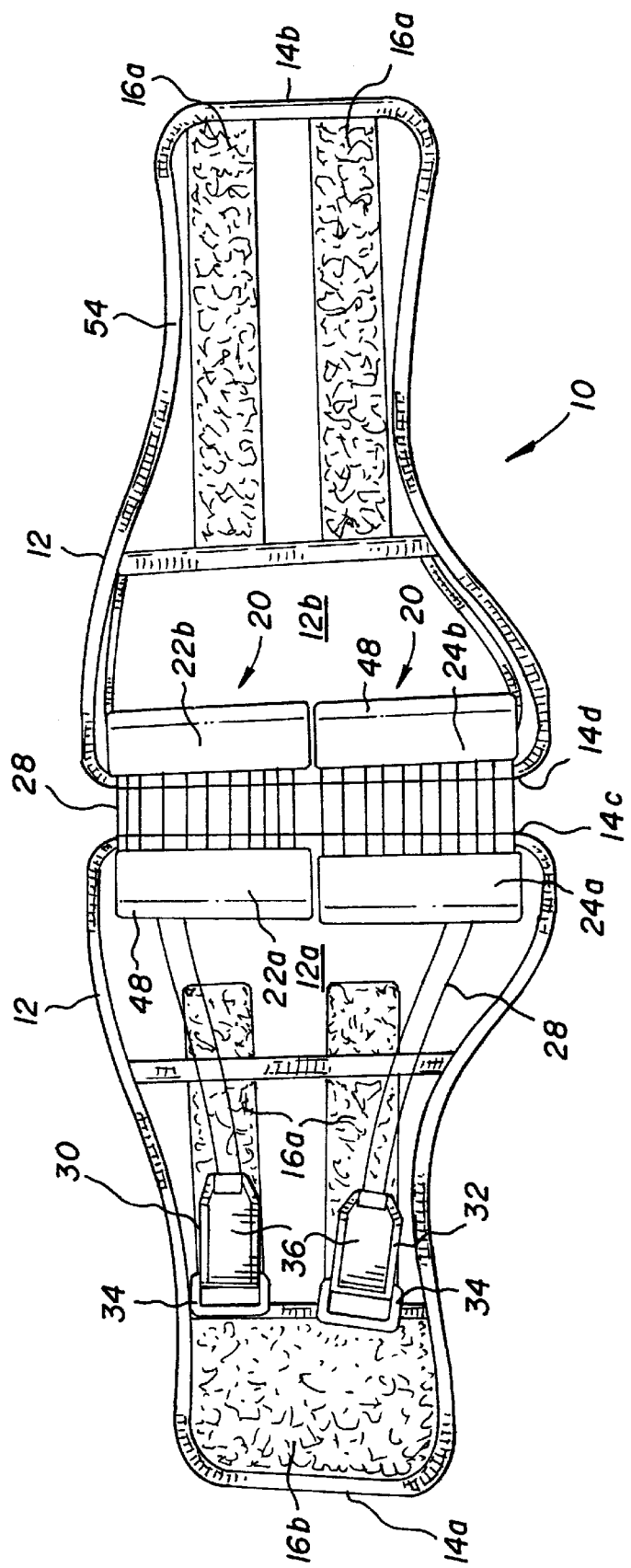
FIG. 1 shows a plan view of an outer side of a first embodiment of an orthotic device according to the present invention.

FIGS. 1–6 show a first embodiment of the present invention. FIG. 1 illustrates the outer side of a body jacket type of back brace 10 in an extended position. The brace 10 includes a brace body 12 made of a material suitable to achieve the type of support sought in treating the condition of the patient wearing the orthotic device. Accordingly, in some situations a softer, more pliant material is preferred where the device is intended to conform substantially to the body of the wearer and provide support but where rigid support is not necessary. In other situations, where flexion is to be avoided, either a more rigid material is selected for all or a portion of the body of the orthosis (such as in body jackets) or the orthotic device is used in conjunction with other component parts made from a more rigid material (such as in thoracic lumbar sacral orthoses). Suitable materials include canvass, nylon, polyethylene, nylon mesh or other similar materials. Where a more rigid orthotic device is sought, rigid polyethylene may be used alone and various combinations of materials may be employed to obtain properties of rigidity and breathability.

It may be noted that the term "rigid", as used herein to describe materials from which the orthoses of the invention are constructed, does not mean totally inflexible or unyielding, since many of materials employed can be bent when a sufficient force is applied to a surface of the material. These materials typically resume their original configurations when the deforming force is removed, however. As used in describing the materials from which the invention is constructed, rigidity refers to a resistance to deformation exhibited when in use, orthoses constructed of such materials are not bent or deformed when someone wearing the device bends in a fore or aft direction or in a lateral direction using a force to move in such direction which is considered not to be excessive for that person.

Figure 2:
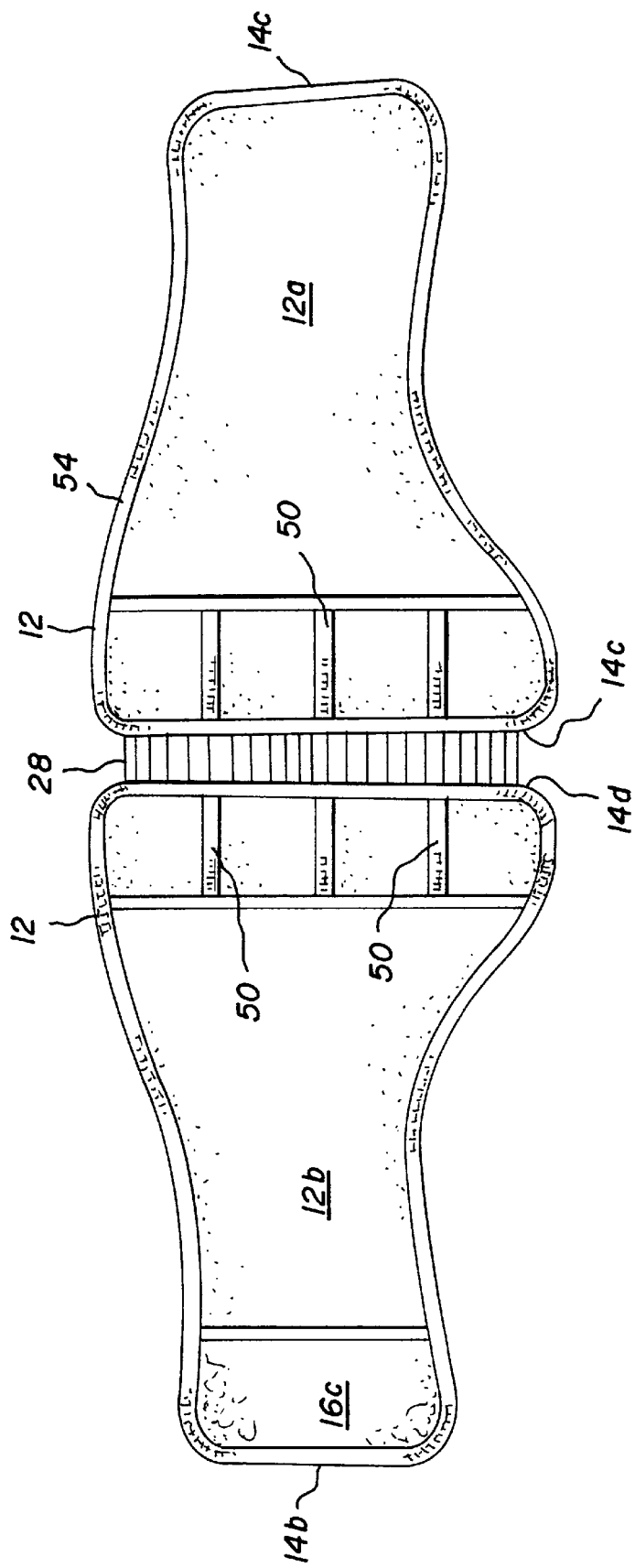
FIG. 2 illustrates a plan view of an inner side of the embodiment shown in FIG. 1.
Figure 6:
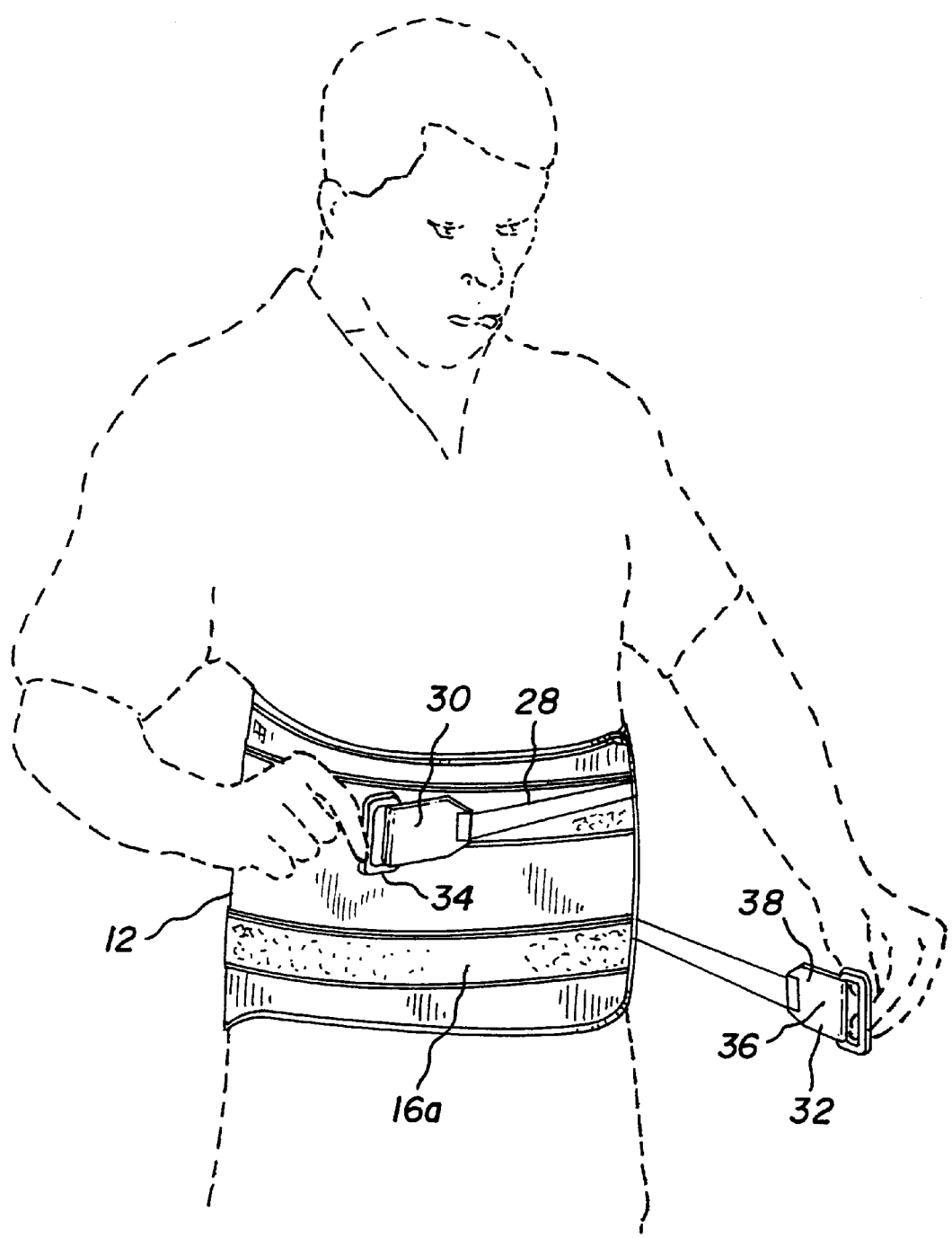
FIG. 6 shows a first embodiment of the invention as it is worn by a patient.

In a preferred embodiment of the brace body 12 illustrated in FIGS. 1, 2 and 6, two brace body segments, 12a and 12b, are shown, each including part of the individual adjuster or tightening means of the orthotic device. On opposite overlapping sides of opposite distal or free ends 14a and 14b of each brace body segment are provided complementary fastener or fastening means for securing the two free ends 14a and 14b together after the brace is wrapped around the patients torso. Although, buttons and button holes, snap fasteners or other similar fasteners commonly used in garments may be employed to secure the free ends of the brace body 12 together, much preferred are complementary sections of hook-and-loop fastener fabric mounted on opposite overlapping sides of opposite body brace segments 12a and 12b at at least the free ends thereof. In a preferred embodiment illustrated in FIGS. 1 and 2, complementary portions of hook-and-loop fabric are represented by numeral 16b and 16c. In addition to such material being capable of withstanding a large amount of shear stress so that the brace 10 may be kept under tension, the portions of the brace body 12 secured to one another may be easily peeled away when the apparatus is to be taken off. Furthermore, such material allows the free ends 14a and 14b to be removably attached to one another in a variety of positions and with the possibility of incremental adjustment, attributes not typically found in fastening systems frequently encountered in garments. In addition to providing such complementary portions of hook-and-loop material at the free ends 14a and 14b of the brace body segments 12a and 12b, respectively, horizontal strips 16a of hook-and-loop are arranged on the exterior surface of each brace body segment to allow for removably securing handles attached to the ends of the cable 28 used in the individual tension adjusters.

The preferred tension adjusters used to custom fit the orthotic devices of the present invention to the profile of the individual wearer of these orthotic devices are shown in preferred embodiments illustrated in FIGS. 1–4. Thus, the preferred means of individual adjustment and custom fitting of the orthotic devices of the invention include at least two independent pulley sets 20. Each set of pulleys includes a pair of opposing banks of pulleys (an upper set including banks 22a and 22b and a lower set including banks 24a and 24b). Each bank includes a plurality of individual pulleys 26 (illustrated in FIG. 4) and a cable 28 is looped serially and in alteration around the pulleys 26 and is fixed at each end of the cable to a controlling device such as a handle, designated as 30 (for the upper set of pulleys that includes pulley banks 22a and 22b) and 32 (for the lower set of pulleys that includes pulley banks 24a and 24b), so as, in effect to form an endless cable. Although a cable which is anchored at one end, wound around each of the pulleys in a series could be used to achieve a suitable mechanical advantage and adjustment to accomplish the same degree of adjustment of the endless cable of a preferred embodiment of the invention, the cable would need to be pulled to twice the length. This is not ergonomically desirable, nor even feasible, for the great majority of patients.

The number of pulleys provided in each bank of pulleys is determined by such factors as the amount of space provided for pulleys within each bank and the mechanical advantage being sought. The size of the particular bank of pulleys is determined in part by the size of the orthotic device and manufacturing considerations. Larger devices allow for concomitantly larger pulley sets and their respective banks of pulleys. The appropriate mechanical advantage is determined with a consideration of the strength of the user or the type of ailment necessitating the use of the orthotic device, the rigidity of the orthosis being adjusted, the volume of the torso covered by the device, portion thereof being adjusted. Generally, each pulley system used in the orthoses of the invention is constructed with an appropriate number of pulleys to provide a minimum of effort to achieve abdominal compression but not high enough to cause injury by over-tensioning the orthosis. Typically, this equates to a mechanical advantage for each pulley system in the range of about 4:1 to about 30:1. For those devices which require less effort to tighten, such as smaller orthoses and those formed from compliant materials such as those used only to treat the lumbar region of a patient, a mechanical advantage of about 4:1 to about 8:1 is preferred. For orthoses which are larger or are constructed at least in part from rigid material, such as body jackets, a mechanical advantage of about 6:1 to about 18:1 is preferred. In orthotic devices which are very large or are substantially rigid because of the rigid nature of the materials from which they are constructed or the number of rigid component parts, such as thoracic lumbar sacral orthoses, a mechanical advantage of about 12:1 to about 30:1 is preferred.

Figure 3:
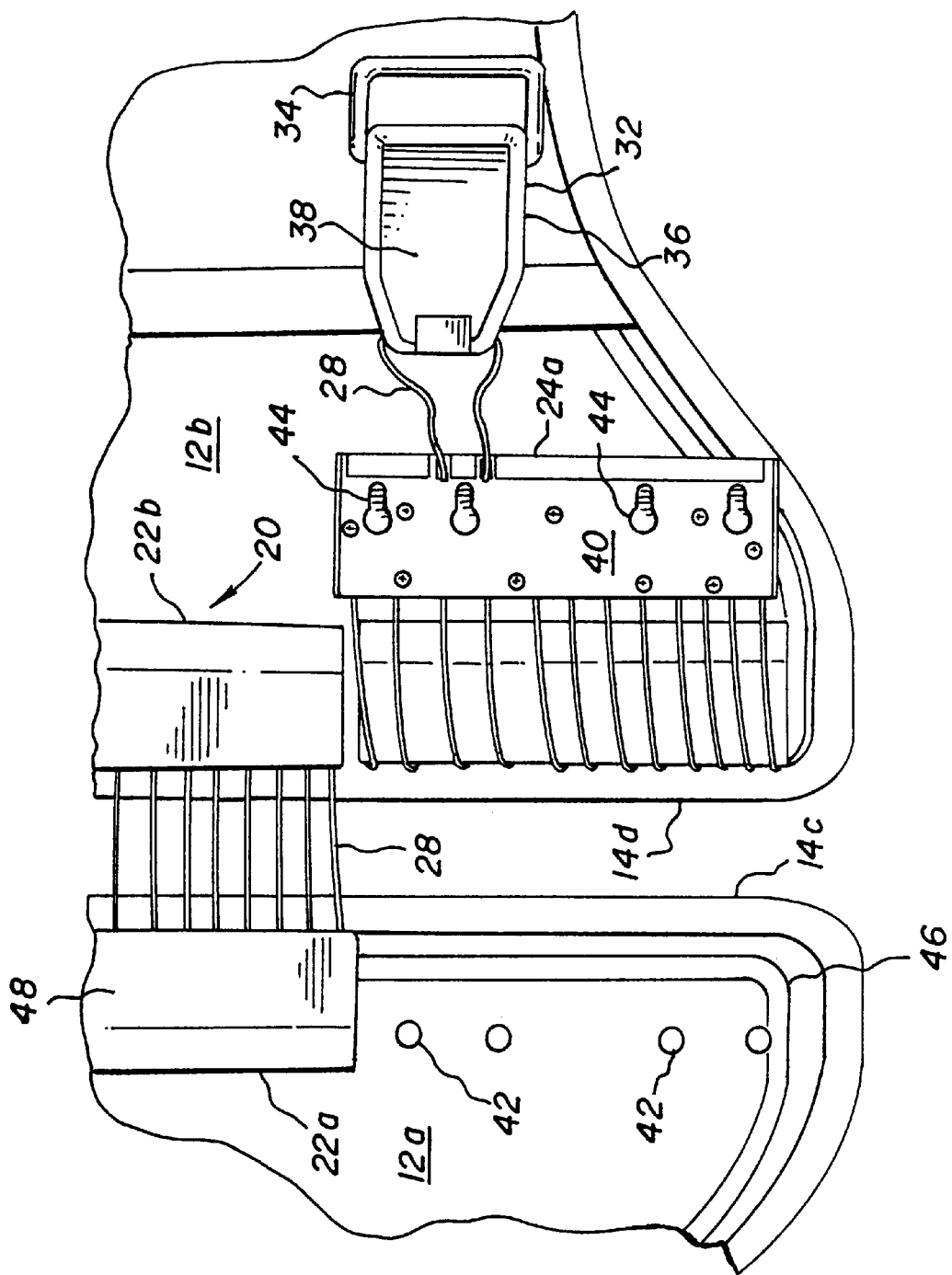
FIG. 3 illustrates an enlarged portion of the embodiment of the present invention illustrated in FIG. 1 with a bank of a set of the modular pulley system removed from its corresponding segment of the orthotic device of the present invention so as to reveal the underside of the bank.

As illustrated in FIGS. 1, 3 and 6, the ends of each cable 28 are preferably attached to a controlling or handle device for each set of pulleys. The device may include an easily graspable member, such as a cloth tab, loop, ring or bail. In the preferred embodiments illustrated in FIGS. 1, 3 and 6, a bail shaped member 34, formed from metal or preferably plastic, either rigid or flexible, is secured or formed as part of a tab member 36. Preferably, the handle also includes a means of detachably securing the handle 30 or 32 to a body brace segment after adjustment has been made or the device has been removed from the wearer. Such means of securing could include a series of clasps or a buckle and strap arrangement. However, most preferred is a hook-and-loop arrangement. In such a system, a piece of hook-and-loop fabric 38 is affixed to the underside of a portion of the handle such as member 36. After adjustment has been made and the appropriate tension has been established in the cable 28, the handle may be releasably secured to a brace body segment 12a or 12b by placing the hook-and-loop fabric portion 38 attached to the handle member 36 in contact with a portion of the complementary hook-and-loop material 16a on the body brace segment 12a or 12b, as illustrated in FIG. 1. When a portion of hook-and-loop material is used as a securing means on the handle it is preferred to use a thin moderately flexible plastic, such as polyethylene, to form the handle can be pulled to and conform to the side of the patient.

Each bank of pulleys 22a, 22b, 24a and 24b of the pulley sets 20 is secured to a portion of a body brace segment 12a and 12b adjacent a juxtaposed body brace segment edge thereof (14c or 14d). The proximate or juxtaposed edges 14c and 14d of the adjacent body brace segments 12a and 12b may be joined together by a portion of flexible pliant material which secures the juxtaposed edges 14c and 14d at opposite edges of the portion of pliant material or the brace body 12 may be formed as a single unitary object including brace body segments 12a, 12b and an intermediate section lying there between. Preferably, however, brace body segments 12a and 12b of the brace body 12 are separate, detached segments joined to one another solely by cable 28. This allows for greater heat dissipation by a wearer and facilitates disassembly and cleaning.

Figure 4:
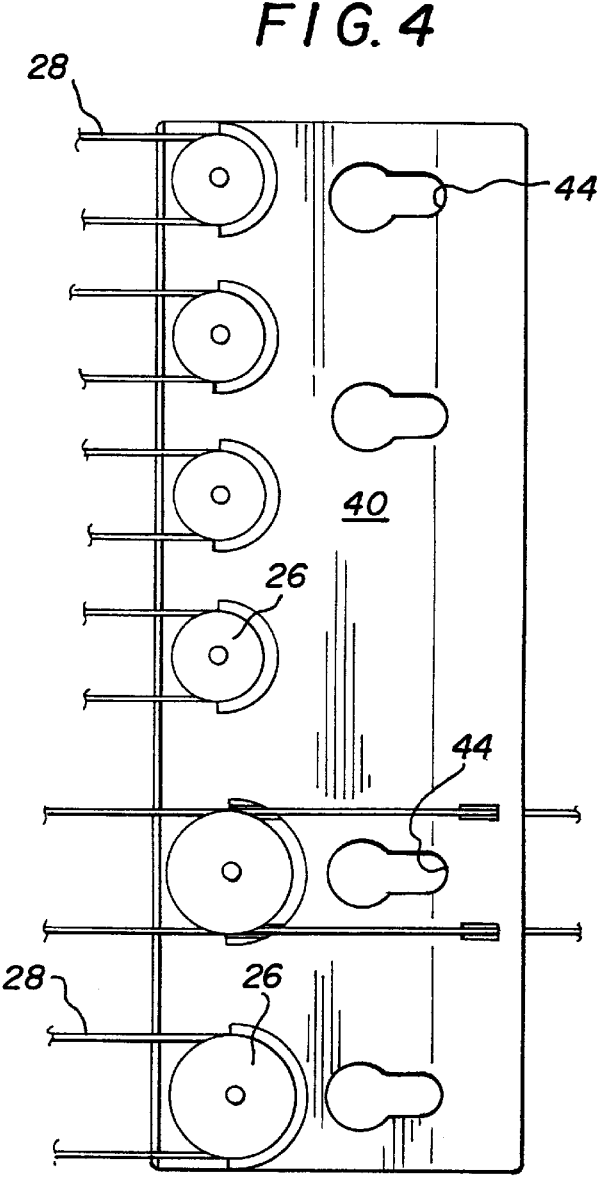
FIG. 4 shows a bank of a modular pulley set employed in a present invention with its cover removed.
Figure 5:
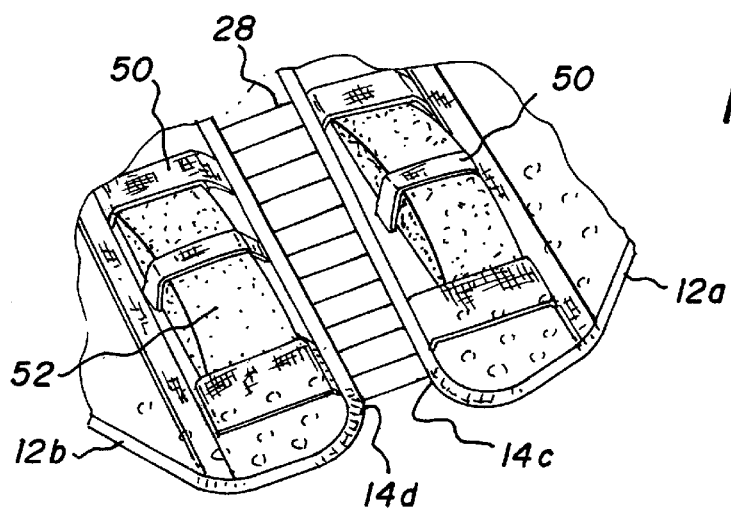
FIG. 5 shows an inner portion of an orthosis according to the invention containing lordotic pads.

Although the individual pulleys may be secured directly to the material from which the brace body 12 is formed, it is much preferred that they are secured to a plate, such as plate 40 illustrated in FIGS. 3 and 4. The plate 40 may be affixed to the material from which the body brace segments are formed by any convenient fastening means, such as rivets, staples, etc. However, it is preferred that each bank of pulleys is formed as a modular unit attached to the other bank of pulleys in the pulley set on the opposing juxtaposed edge (14c or 14d) of the opposing brace body segment by means of one of the cables 28. As a modular unit, the plate 40 is detachably secured to a brace body segment 12a or 12b by any convenient detachable fastening means, such as complementary tabs and slots, hook-and-loop fabric, etc. Preferably, however, mushroom shaped rivets or pins 42 having an exposed flanged portion are placed near the edge portions 14c and 14d of each brace body segment. Plates 40 of each pulley bank 22a, 22b, 24a, and 24b, are provided with commensurately shaped and spaced key hole-shaped slots 44 which detachably engage mushroom-shaped pins 42. The dimensions of the narrow portions of each of the key hole-shaped slots 44 are such that the plates 40 of each of the modular banks of pulleys may be detachably mounted or dismounted on the pins 42 by applying a suitable amount of hand pressure. To provide additional reinforcement, the pins may be affixed to a separate flap 46 secured to the main brace body segment 12a or 12b. Preferably flap 46 is made from a material having high tensile strength which resists tearing and the pins 42 being pulled from the flap. Preferably, the flap 46 has a rigidity equal to or greater than the main portion of the body brace segments 12a and 12b.

Although each of the pulleys in a bank may be of the same size and spaced from the next adjacent pulley, a greater force is achieved. Accordingly, in situations where the nature of the anatomy varies in the area over which the pulley set extends, an embodiment such as that illustrated in FIG. 4 may be preferred. Thus, pulleys with larger diameter spools and/or larger center-to-center distances between spools may be placed at one end of the pulley bank and the band may be oriented such that the portion of the bank in which smaller pulley spools are located and/or where the center-to-center distance between spools is smaller is proximate to or superposed on the region of the anatomy where the greatest resistance to compression exists.

By forming the pulley sets 20 as modular units which may be detachably secured to the brace body segments 12a and 12b or flaps 46, allows facile removal of the component parts of the orthotic device for cleaning. In addition, in the arrangement of the orthosis shown in FIG. 1, the pulley sets are so arranged that pulley bank 22b is arranged above pulley bank 24b with handles 30 and 32 arranged to extend to the same side of the orthosis and the same brace body segment 12b. This is a typical arrangement for most wearers of body braces (as shown in FIG. 6) since most individuals exhibit greater strength in their dominant arm. However, based on individual preference or where comparable strength exists in each arm, some users may prefer an arrangement in which each arm controls one of the cables attached to one of the handles 30 or 32, to allow individual adjustment of each pulley set 20. This may be easily accomplished with a preferred embodiment of the invention in which modular pulley sets are employed since the individual pulley banks may be detached from their corresponding pins and the pulley set rotated 180° in the plane of the extended orthosis to allow reattachment of the pulley set 20 such that the handle 30 or 32 of the pulley set being repositioned is arranged to extend over the opposite brace body segment.

Each pulley bank 22a, 22b, 24a and 24b includes a cover 48 removably attached to the base plate 40 by any convenient fastener means, such as screws, bolts, recesses and engaging tabs, etc.

To apply appropriate support and pressure to portions of the spine, as required by the patients condition, a preferred embodiment of the invention (FIG. 5) includes appropriately configured lordotic pads 52, provided to adjust for lordosis, for the lower curve of the back. These pads are positioned on the interior of the orthotic device 10 adjacent the abutting edges 14c and 14d. Although such pads may be permanently retained in the device by sewing in place and/or by covering with a suitable material, it is preferred that they be removably retained in the brace by transverse elastic straps 50 disposed at positions on brace segments 12a and 12b which allow the straps to transversely contact and hold each pad at approximately the ends and mid points of each orthotic pad. Preferably, each pad is formed from a high density compressible, elastic foam material.

Although in many applications it may be unnecessary to provide a lining on the interior surface of the brace body 12, to achieve additional comfort, a liner is preferred, and most preferred is one made of compressed foam. Preferably the liner is easily cleaned and most preferably is removable for cleaning. A particularly preferred liner is a perforated foam containing a "waffle" pattern in which the pattern is defined by interconnecting channels or troughs that intersect at the apertures to provide air circulation next to the body. A nylon mesh may be used over the foam liner to provide increased rigidity as well as breathability.

In using this embodiment of the invention, the wearer merely places the device 10 around the waist with the portion of the body brace 10 having the pulley sets 20 arranged on the exterior surface and to the rear of the user. The free ends 14a and 14b are arranged one over the other in appropriate engagement. In the preferred embodiment, this involves engaging the appropriate hook-and-loop portions in facing relationship. Once the orthotic device is secured around the torso, the wearer may then separately pull each of the handles 30 and 32 to adjust the tension of the device to provide the degree of comfort and conformity of the brace provided by the separate adjustments of the pulley system. After adjustment, the wearer merely presses the side of the handle with the hook-and-loop material thereon against the complementary hook-and-loop strip 16*a* on the brace body 12. When the user changes body positions, tension of the individual pulley systems and of the overall brace may be subsequently readjusted.

Although the orthotic devices of the present invention permit custom fitting and adjusting over a wide range of dimensional variables, it is preferred to provide the present invention in a range of sizes to permit an orthotist to tailor individualized fitting of the devices to a wide range of individuals within different size and profile ranges. In a preferred embodiment of the invention, an edge or bias binding 54 is provided to prevent the materials from which the brace body 12 is formed from fraying or, where several layers, such as a nylon mesh and/or rigid outer layer and/or a foam cushioning liner are provided, from separating of the adhered or laminated layers. In another preferred embodiment of the invention, the orthoses do not include a bias binding, thereby permitting the orthotist to cut the brace body in order to custom fit the device to the user.

Figure 7:
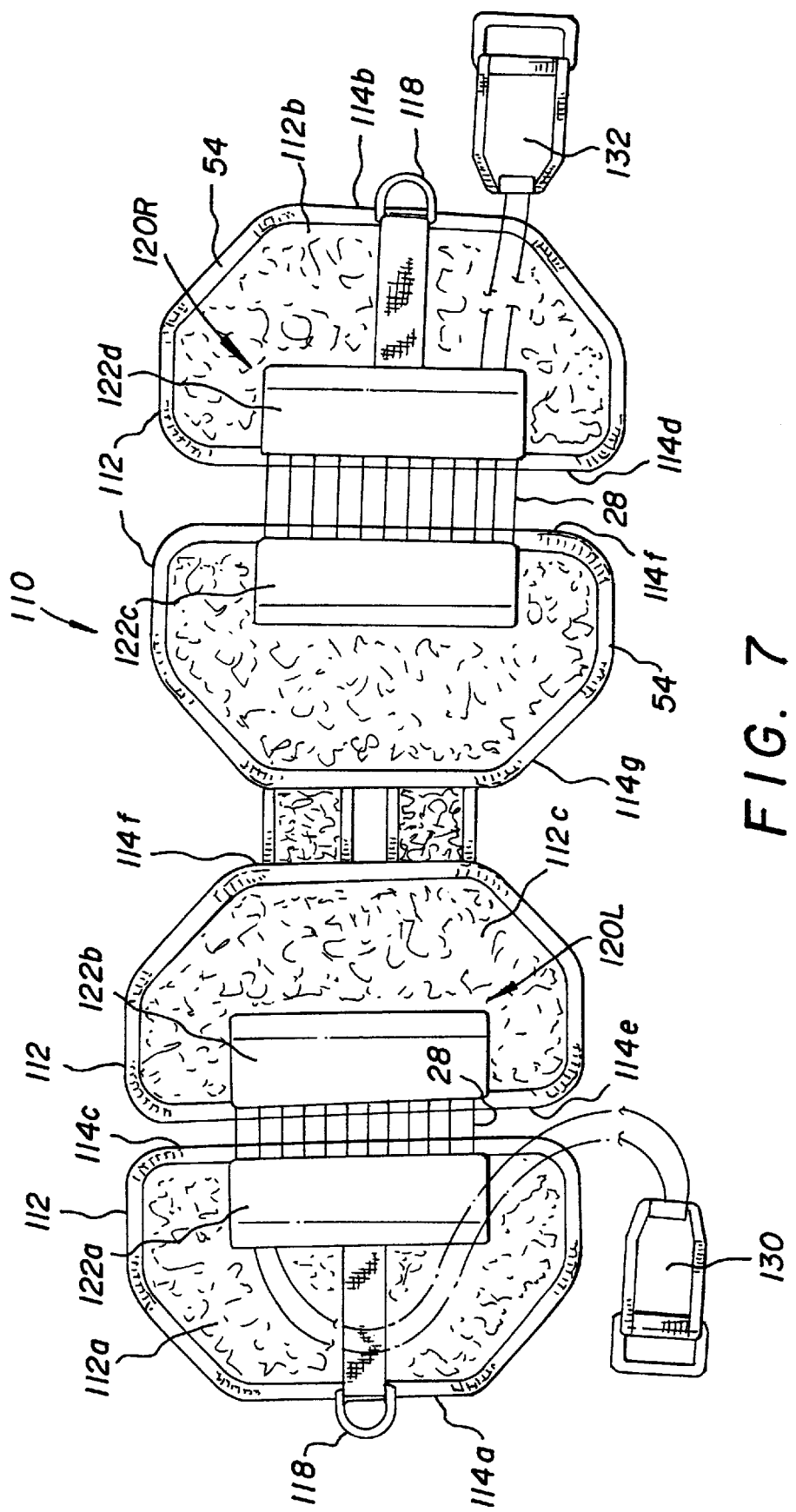
FIG. 7 shows a plan view of the outer side of a second embodiment of an orthotic device according to the present invention.
Figures 10, 11:
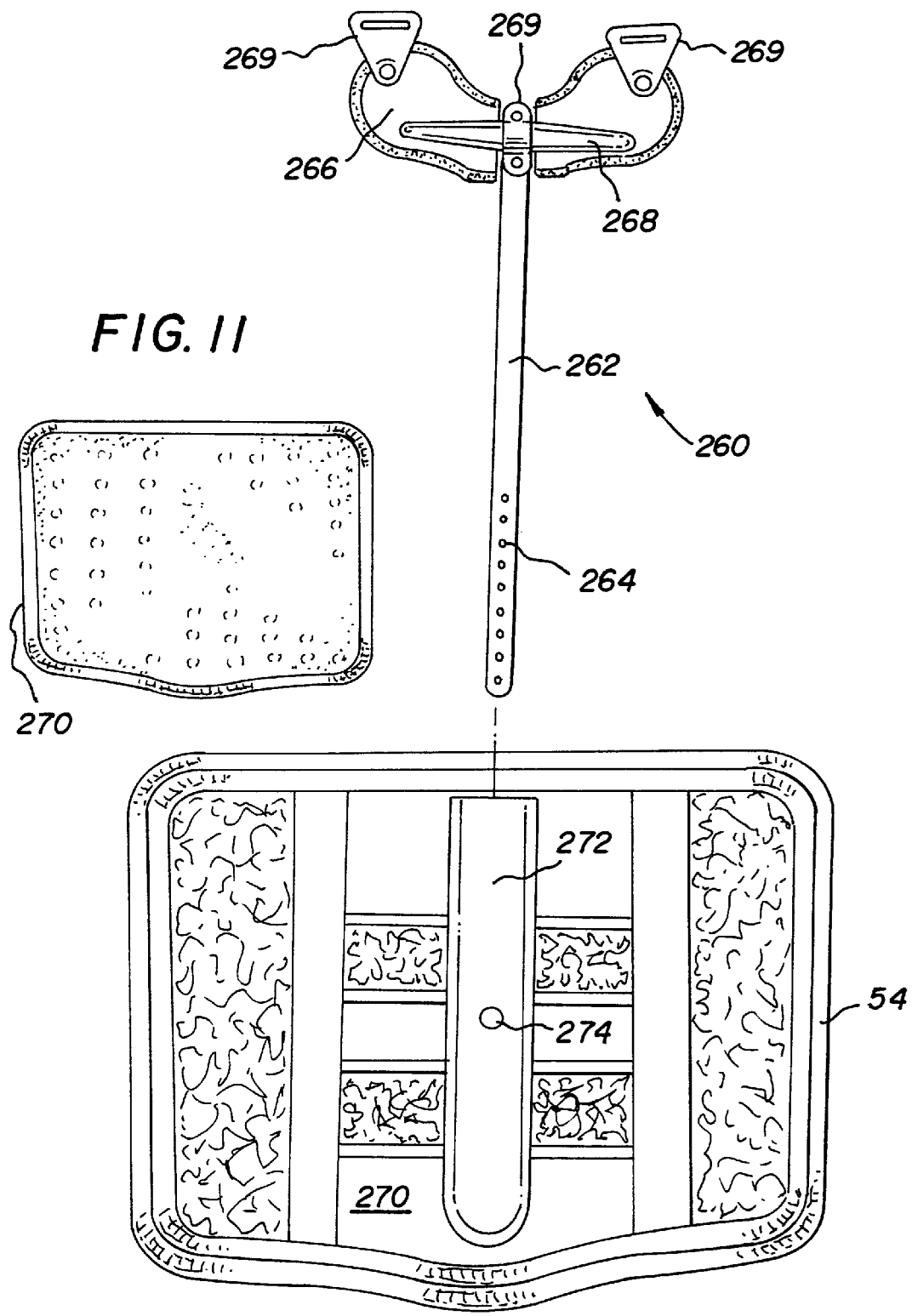
FIG. 10 shows the outer or front side of a front component piece of a TLSO and a sternal notch piece received by the front piece according to the present invention.
FIG. 11 illustrates an inner side of a front component piece illustrated in FIG. 10.

Another embodiment of the invention is shown in FIG. 7. Although similar to the first embodiment in a number of respects, including the provision of a plurality of adjustment means, particularly preferred being a plurality of pulley sets, the arrangement of the pulley sets and the number of segments of the brace body differ from the first embodiment. In this embodiment, the same reference numerals are used to represent the same or similar elements as represented in the embodiments illustrated in FIGS. 1–6. FIG. 7 shows a plan view of the exterior or outer side of a second embodiment of the back brace apparatus in an extended position. The brace 110 includes a brace body 112 made of the same or similar materials discussed above with respect to the first embodiment of the invention illustrated in FIGS. 1–6. In the embodiment of the invention illustrated in FIG. 7, although two pulley sets 120L and 120R are employed, rather than being arranged vertically, one above the other, as in the embodiment illustrated in FIGS. 1–3, this embodiment includes an arrangement where the pulley sets are disposed horizontally and laterally. In contrast to the first embodiment in which the pulley sets 20 are arranged vertically and tension originates at the rear portion of the brace by individually tightening the posteriorly arranged pulley sets, the second embodiment of the invention includes pulley sets 120L and 120R which are arranged laterally and which are disposed at the sides of the device when the orthotic device 110 is placed on the torso of the user. In addition, in contrast to the minimum of two brace body segments 12*a* and 12*b* of the brace body 12 illustrated in FIGS. 1 to 3, the brace body 112 of the second embodiment, illustrated in FIG. 7, includes a minimum of 3 brace body segments: a central brace body segment 112*c,* intended to be placed surrounding the rear and the sides of the wearer and two distal or free end brace body segments 112*a* and 112*b,* arranged in symmetrical and juxtaposed relationship to central brace body segment 112*c* and intended to be placed surrounding the sides and anterior portion of the torso. Each of the brace body segments 112*a,* 112*b* and 112*c* may be joined by flexible, pliant material, formed as a unitary structure from the same piece of material or may be formed as separate component parts, such as the options existing for the first embodiment of the invention. Preferably, brace body segments 112*a,* 112*b* and 112*c* are formed as separate segments for reasons similar to those mentioned above for the first segment The posterior segment 112*c* may be formed as a single unit or, as illustrated in FIG. 7, preferably as two units joined at opposing edges 114*f* and 114*g.* This reduces weight and permits better heat dissipation.

The pulley sets 120L and 120R each consist of two pulley banks which provide a means of adjusting the tension and distance between the posterior brace body segment 112*c* and in each set one of the two free end segments 112*a* and 112*b*. Thus, pulley 120L includes pulley bank 122*a,* attached to brace body segment 112*a* adjacent edge 114*c* and pulley bank 122*b,* attached to proximate, juxtaposed brace body segment 112*c* adjacent edge 114*e*. A cable 28 runs serially and in alteration through the pulleys of each of the pulley banks 122*a* and 122*b,* thereby operatively connecting each of the banks in the pulley set 120L. The ends of the cable are attached to a handle, such as handle 130 which is provided with features similar to handle 30 of the first embodiment. Likewise, pulley set 120R includes pulley banks 122*c* and 122*d,* affixed to proximate, juxtaposed facing portions of brace body segments 112*c* and 112*b,* respectively, at juxtaposed edges 114*f* and 114*d,* respectively. A cable 28, operatively connects the cable banks of 122*c* and 122*d* of pulley set 120R serially and in alteration, the ends of cable 28 being attached to a handle 132 similar to or the same as handles 30 and 32 of the first embodiment or 130 of this embodiment. Since the pulley sets in this embodiment are arranged horizontally and laterally rather than vertically, one above the other, as in the first embodiment, it is preferred that the pulley sets 120L and 120R, and their concomitant handles 130 and 132, be so arranged that they are pulled from opposite sides of the body rather than the same side of body. However, where the condition of the user so requires, and where the preferred embodiment of the device includes modular pulley sets, preferred as in the first embodiment, one of the pulley sets may be detachably removed from its respective brace body and rotated 180° in the plane of a brace body segment so that both handles may be pulled from the same side of the body.

Orthotic device 110 may be provided with similar fastening or closure means as used in the orthosis 10. Preferably, the means for both closure and fastening around the torso of the individual, as well as gross adjustment of the device, and preferably for securing of the individual handles 130 and 132 is provided by hook-and-loop fabric portions. As in the first embodiment, the hook-and-loop portions used for fastening and gross adjustment of the device may be provided at the free or distal ends of the brace body segments such that they are in superposed relationship when the free ends overlap. In the embodiment shown in FIG. 7, the portions of hook-and-loop material are provided near the free edges 114*a* and 114*b* at appropriate positions and on the interior and exterior surfaces of the device and also appropriately positioned to detachably secure handles 130 and 132. In addition, edges 114*a* and 114*b* of brace body segments 112*a* and 112*b,* respectively may be configured more closely to the shape of edges 14*a* and 14*b* of the first embodiment illustrated in FIGS. 1 and 2, particularly when orthosis 110 is used as a stand alone device. That is, edges 114*a* and 114*b* may be shaped in the form of projecting tabs which allow brace body segments 112*a* and 112*b* to more fully overlap one another and more easily engage a fastening and closure means provided at the free ends of these segments. The configuration of the free end brace body segments 112*a* and 112*b* shown in FIG. 7 are quite compatible, however, with another embodiment of the invention discussed below.

As indicated above, depending upon the particular ailment or medical condition of the patient, the orthoses of the present invention my be formed from either flexible materials or rigid materials. In both of the previously discussed embodiments of the invention, when a rigid body jacket is desirable, either portions of, or the entire device, may be formed of a rigid plastic material, in which the rigidity of the plastic is selected based upon the amount of patient body flexure which can be tolerated for the ailment or prescribed treatment procedure of the user of the device. In many instances, all or a portion of the orthosis, particularly the rear portion of the device, is formed from a rigid plastic material. This is true for rigid body jackets. In many instances, as a result of surgery, forward flexure of the patient is to be minimized or substantially eliminated. In such instances, a physician may prescribe a thoracic lumbar sacral orthosis (TLSO), which is intended to prevent forward flexure of the upper portion of the torso. The body braces of the present invention may be used with additional component parts to form TLSOs which are both easily donned and doffed and include multiple means of adjustment which allow the devices to be individually and separately adjusted to provide extensive posterior and anterior adjustment options, as well as assuring that certain portions of the body brace conform to the profile and body dimensions of the wearer. Although the preferred TLSO orthosis of the invention is discussed herein in terms of a combination with the body brace device 110, shown in FIG. 7, it should be understood that similarly constructed and arranged devices, discussed below, may also be used in conjunction with all of the body braces discussed herein, such as body brace 10.

Figure 12:
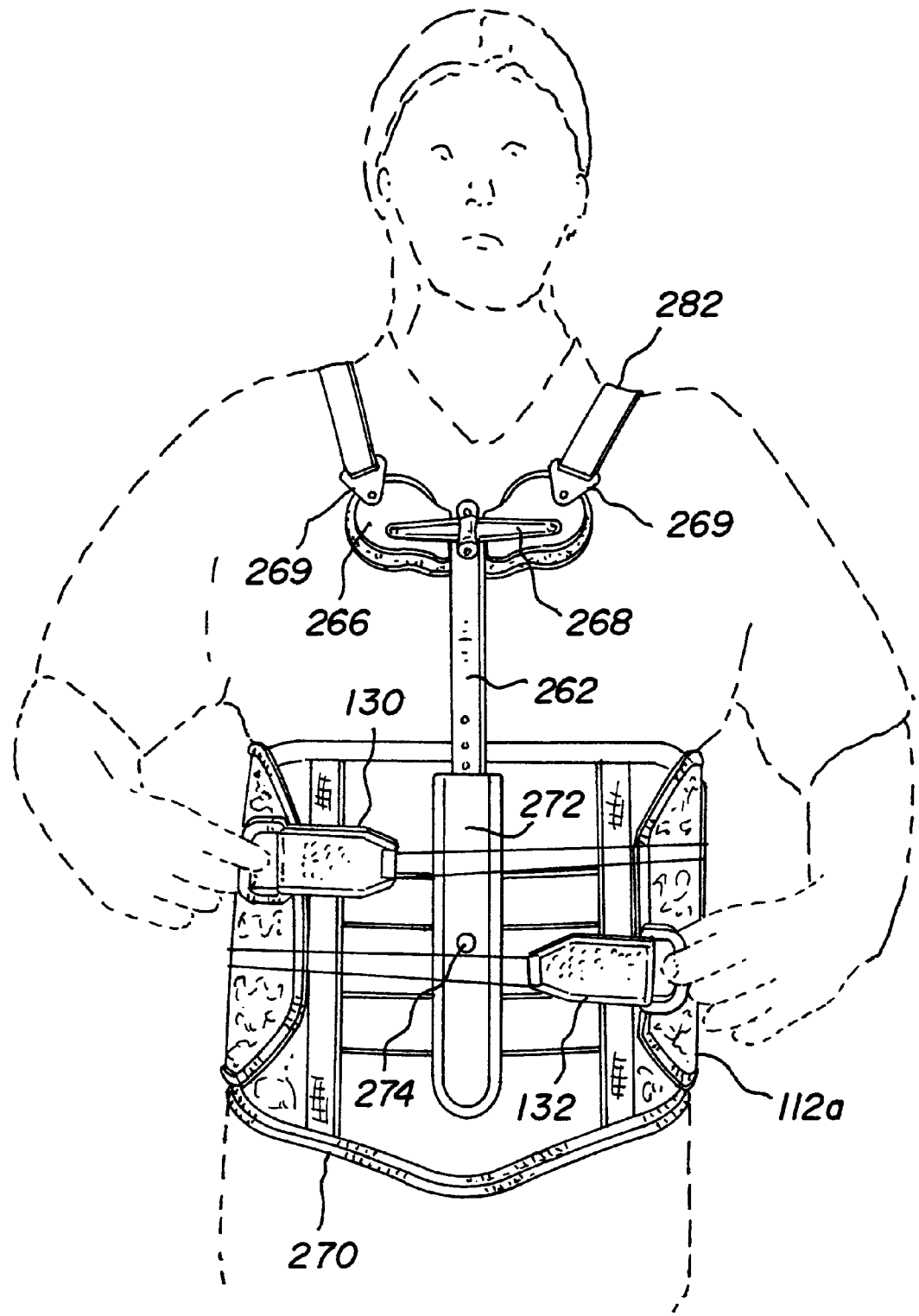
FIG. 12 shows a front view of the orthotic device of FIGS. 8, 9, 10 and 11 as it is worn by a patient.
Figure 13:
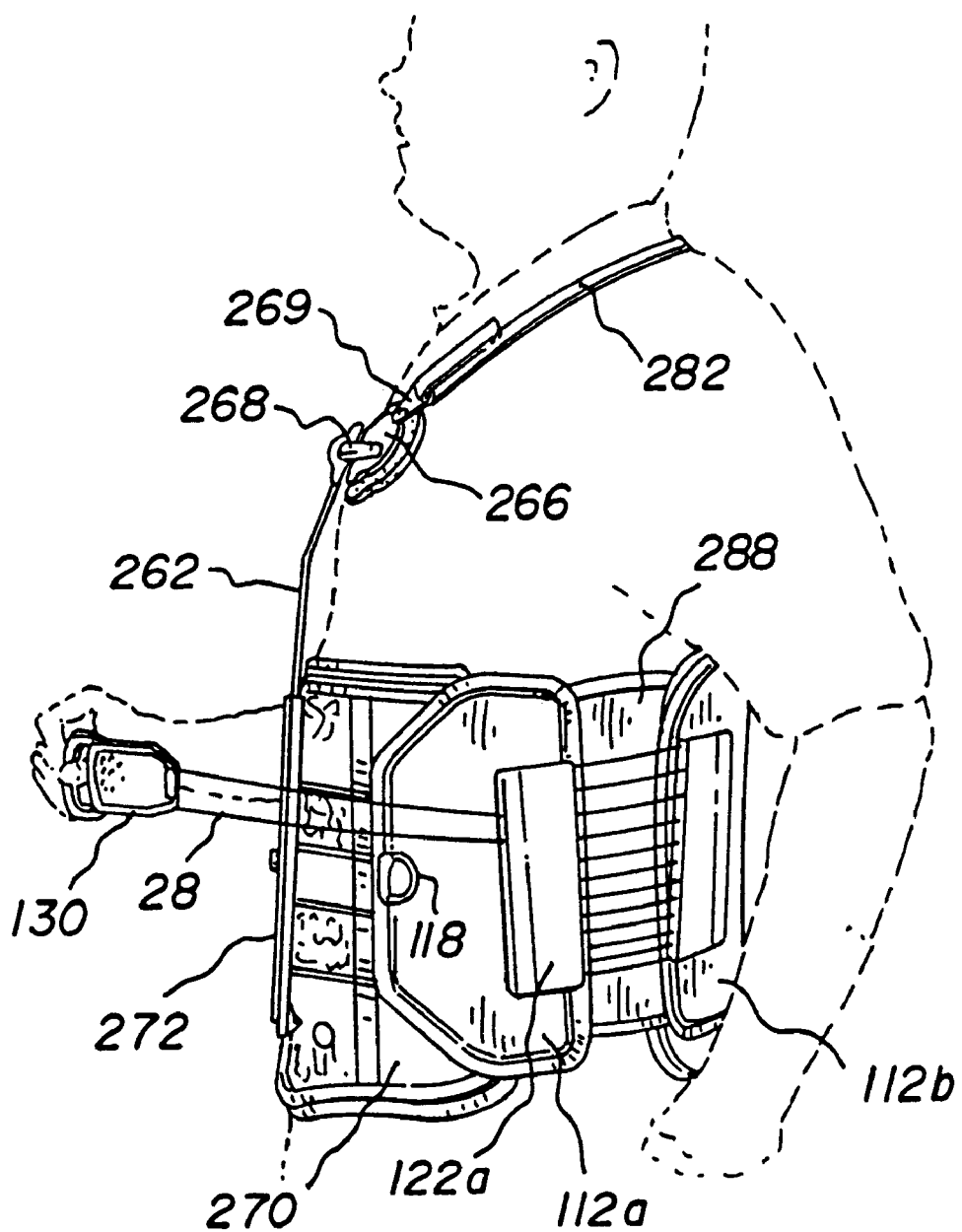
FIG. 13 shows a side view of the orthotic device of FIGS. 8, 9, 10, 11 and 12 as it is worn by a patient.

The three component parts used in addition to and in conjunction with the previously described body brace type of orthotic devices of the invention to form the TLSO devices of the invention include the component parts illustrated in FIGS. 8 to 11. These components include sternal notch piece 260, shown in FIGS. 10, 12 and 13. The sternal notch piece 260 includes a rigid adjustment piece 262 formed form a metal such as steel or a rigid high tensile strength plastic. The adjustment piece 262, formed as a post, is provided with adjustment apertures 264 to allow positioning of the sternal notch piece. Attached to the upper portion of the adjustment piece 262 of the sternal notch piece is a body connecting piece, 266, formed as one or two segments intended to contact the sternum region of a patient when the TLSO is worn. On the inner surface of the body contacting piece 266 is affixed compressible elastic foam pads (not shown). The body contacting piece 266 is pivotally secured to the post 262 by means of a hinge-like arrangement including a rod or a spindle 268 disposed transverse the body contacting piece 266 and formed as part of or secured at the rear thereof at both ends of the rod 268, the rod being in turn secured to the adjustable post 262 by means of a sleeve and/or clamp 269 attached to the adjustment piece 262 and which encircles the rod 268 at approximately its midpoint.

A substantially rigid breast plate or front piece 270 (shown in FIGS. 10 and 11) is used to movably secure the sternal notch piece 260 to the TLSO. Front piece 270, formed from a rigid plastic material, such as polyethylene, includes an adjustment piece receiving portion 272 arranged vertically in the front piece. The adjustment piece receiving portion 272 includes a channel formed therein (not shown) commensurate in shape and length to slidably receive adjustment post 262 of the sternal notch piece 260. Placed intermediate the channel entranceway of the adjustment piece receiving portion 272, and the bottom of the adjustment piece receiving portion 272 is provided an aperture engaging device 274 intended to engage adjustment apertures 264 of the adjustment post 262. Preferably, the aperture engaging device 274 is a mushroom-shaped spring loaded pin, the free end or tip of which may be retracted partially from the post receiving portion channel against the tension of the spring by pulling outwardly on the exposed head of the pin to disengage the tip of the pin from apertures 264. Release of the pin to a biased position permits engagement of the tip of the pin 274 with a specific aperture 264. By pulling outwardly on the pin 274, the pin is released from an aperture and the adjustment post 262 may be slidably repositioned and the pin therefore released in order to bias against the adjustment post. If the pin does not immediately engage an aperture 264 in the post 262, the post may be raised or lowered to the nearest suitable position.

At the lateral upper portions of the body contacting piece 266 are located strap engaging members 269, formed preferably as slotted tabs which are pivotally secured to the body contacting pad 266 such that they rotate substantially in the plane of the pads. The strap engaging members 269 are intended to engage or retain straps 282 (shown in FIGS. 8, 9, 12 and 13), which are secured to a back piece 280 by strap retainers 284, which may be the same or similar to strap engaging members 269, thereby removably securing the front piece 270 to the back piece 280. The straps or belts 282 include buckles or other adjustment means (not shown) which allow for gross adjustment to fit the wearer of the orthotic device. The distal or free ends 286 of the straps 282 pass through the slots of the strap retainers 269 of the body contact pieces 266. The straps 282 and/or the free ends 286 of the straps include fastening means (not shown) to secure the straps 282 which have passed through the strap retainers 269. Suitable fasteners including buckles, snaps or, preferably, complementary hook-and-loop fabric fasteners, secured at appropriate positions to the straps, such that when the free ends of the straps have passed through the slots of the strap engaging members 269 and folded back on themselves, they are removably secured thereto.

The back piece 280 may be formed from materials similar to those from which the front piece is formed. Each of the front and back pieces is preferably formed from a rigid plastic material that yields to bending under sufficient pressure but which has a memory and springs back to its original shape when pressure is released. The rigidity of the front piece 270 and back piece 280 must be sufficiently high that when the TLSO is properly placed on the patient in combination with a body brace of the invention, and the sternal notch piece 260 is appropriately adjusted, forward movement of the torso, particularly the upper part of the torso, is minimized or prevented. Plastic materials such as nylon and polyethylene are preferred. Portions of the front piece 270 or back piece 280 may also include a mesh material, such as nylon mesh to provide breathability. Both the front piece and the back piece may include a cushioning liner at the surface of the component pieces intended to be placed in contact with the wearer. Preferably the cushioning liners are formed from a dense, substantially non-compressive type of foam and preferably have a foraminous waffle structure, preferably of the type discussed above. Such liners may be formed or laminated to the inner surfaces of the front piece 270 or back piece 280 or may be formed as separate removable liners which are detachably secured to the interior surfaces of the front piece 270 and the back piece 280 by suitable fasteners such as snaps or complementary portions of hook-and-loop material. It is preferred that the removable feature be incorporated into the device to permit ease of cleaning.

As illustrated in FIGS. 7 and 8, the back piece 280 is provided with two lateral wing portions 288 having a cross-sectional configuration that is generally curved to broadly conform to the size of a human torso. Each of the lateral wing portions 288 is formed from a moderately rigid plastic material, such as nylon mesh to increase breathability, and which has a configurational memory, in that it may be temporarily bent or flexed to a substantial degree but it reverts its original configuration when forces causing such temporary deformations are removed.

The inner surface of the back piece (as shown in FIG. 8) includes elastic retention straps 250 sewn at appropriate locations to allow for the retention and removal of lordotic pads of the type discussed above in connection with the first embodiment of the invention. Front piece 270 and back piece 280 may be provided with detachable retaining means and/or fasteners proximate to the lateral edges thereof such that the body brace 110 (or 10) is retained in the appropriate position when the TLSO is assembled. Preferred are strips of hook-and-loop material 271 and 281 placed on the exterior surfaces proximate to the lateral edges of the front and back pieces 270 and 280, respectively. These strips of hook-and-loop material engage complementary portions of hook-and-loop material adhered at appropriate corresponding locations on the interior surface of the body brace 10 or 110.

When preferred embodiments of the invention are employed, the adjustment piece 262 of the sternal notch piece 260 is placed in the channel of the front piece 270. The straps 282 of the rear piece 280 are threaded through the slots of the strap retention pieces 269 and secured, thereby joining the front piece 270 to the rear piece 280.

In using the TLSO devices of the present invention, the TLSO component parts e.g., the front piece 270, sternal notch piece 260 (FIG. 10) and back piece 280 (FIGS. 8 and 9), are joined and thereafter the assembled components are placed on the wearer. The components are adjusted to the wearer, as indicated above, and a body brace, preferably body brace 110, is fitted around the torso of the wearer and secured in place with the fastening means provided. When an embodiment of the invention that includes a hook-and-loop fastening system is employed, the body brace 110 is merely pressed in place to secure the orthosis. To doff the device, of a body brace end segment, lateral edge such as 114*a* or 114*b*, is pulled away from the front piece 270 and the donning process is reversed. To assist in the removal process, a preferred embodiment provides a grasping member such as D-shaped ring 118 held in place with a strip of cloth sewn in place at lateral edges of each body brace end segment (e.g., 114*a* and 114*b*). The D-shaped rings 118 allow the wearer to firmly grasp and pull the edges more positively.

What is claimed is:

1. An orthotic device comprising:
    an orthosis body adapted to be wrapped around a torso of a wearer of the device, the orthosis body having at least two segments in juxtaposed relationship;
    means provided at free end portions of said at least two segments to releasably secure said free end portions to one another;
    at least two cables, each cable operatively connected to said at least two segments;
    at least two sets of pulleys mounted on said at least two segments with each cable operatively connected to said at least two segments running through a pulley on each of said at least two segments in alteration, shortening of each cable pulling said at least two segments together and tightening the orthotic device with the aid of a mechanical advantage dependent upon the number of pulleys mounted on each said at least two segments; and
    at least two handle elements connected to respective ones of said at least two cables,
    wherein after the means releasably secures said free end portions of the at least two segments to one another, the wearer pulls each of said handle elements a selected distance thereby pulling said at least two cables causing said orthosis body to tighten about the wearers torso to a level of tightening desired by the wearer said at least two handle elements operative for releasable fastening on either one of said releasably secured segments to retain said orthosis body at the desired level of tightening.

2. An orthotic device according to claim 1, wherein said at least two segments comprise two segments, said at least two sets of pulleys comprise two sets of pulleys and said at least two cables comprising two cables.

3. An orthotic device according to claim 2, wherein said two sets of pulleys are disposed vertically with respect to each other at juxtaposed edges of said two segments.

4. An orthotic device according to claim 2, wherein each cable is operatively associated with a separate set of pulleys.

5. An orthotic device according to claim 4, wherein each set of pulleys with an associated cable provides a mechanical advantage of about 4:1 to about 30:1.

6. An orthotic device according to claim 1, wherein each set of pulleys comprise two banks of pulleys and each bank of pulleys of a set of pulleys is mounted on a juxtaposed edge of an adjacent segment.

7. An orthotic device according to claim 6, wherein each bank of pulleys includes a plate on which pulleys are mounted, said plate being detachably mounted on a segment of said at least two segments.

8. An orthotic device according to claim 1, wherein each of said at least two cables is an endless cable.

9. An orthotic device according to claim 1, wherein said detachable securing means comprise portions of hook-and-loop fastener material disposed on overlapping portions of said free end portions of said at least two segments.

10. An orthotic device according to claim 1, wherein at least a portion of each of said at least two segments is formed from a rigid material.

11. An orthotic device according to claim 1, wherein said at least two segments comprise at least three segments, said at least two sets of pulleys comprise two sets of pulleys and said at least two cables comprise two cables.

12. An orthotic device according to claim 11, wherein said at least three segments comprise at least one central segment having first and second opposed lateral edges, at least one first lateral segment disposed at said first opposed lateral edge of said at least one central segment and at least one second lateral segment disposed at said second opposed lateral edge.

13. An orthotic device according to claim 12, wherein said two sets of pulleys are disposed horizontally with respect to each other and includes a first set of pulleys mounted on said at least one central segment and said at least one first lateral segment, and a second set of pulleys is mounted on said at least one central segment and said at least one second lateral segment.

14. An orthotic device according to claim 12, wherein each free edge of said at least one first lateral segment and said at least one second lateral segment has a grasping element attached thereto.

15. An orthotic device according to claim 11, wherein each cable is operatively associated with a separate set of pulleys.

16. An orthotic device according to claim 15, wherein each set of pulleys with an associated cable provides a mechanical advantage of about 4:1 to about 30:1.

17. An orthotic device according to claim 1, wherein each handle element has mounted thereon a portion of a hook-and-loop material complementary to a portion of a hook-and-loop material disposed on an outer surface of said at least two segments.

18. An orthotic device according to claim 17, wherein said handle element is formed from a flexible material.

19. An orthotic device according to claim 1, wherein lordotic pads are mounted at inner surfaces of the orthosis body, symmetrically and at substantially the center of the orthosis body.

20. An orthotic device according to claim 1, wherein each set of pulleys comprise two banks of pulleys, each bank of pulleys including at least one pulley having a spool diameter different in size than remaining pulleys in the set.

21. A thoracic lumbar sacral orthosis comprising:
a rigid front piece;
a sternal notch piece, movably and adjustably secured to said rigid front piece;
a rigid rear piece, removably and adjustably secured to said rigid front piece; and
a body brace comprising:
a brace body adapted to be wrapped around a torso of a patient, said front piece and said rear piece, said brace body comprising at least two brace body segments;
means provided at free end portions of said at least two brace body segments for detachably securing the two free end portions together around the patient's torso;
at least one cable operatively connected to said at least two brace body segments;
at least one set of pulleys mounted on each of said at least two brace segments with the cable running through a pulley on each segment in alteration, shortening of the cable pulling the at least two brace body segments together and tightening the body brace with the aid of a mechanical advantage dependent upon the number of pulleys mounted on each of said at least two brace body segments; and
at least one handle element connected to said at least one cable,
wherein after said means detachably secure said two free end portions of said at least two brace body segments together, the patient pulls each of said at least one handle element a selected distance thereby pulling said at least one cable causing said body brace to tighten about the patient's torso to a level of tightening desired by the patient, said at least one handle element operative for releasable fastening on either one of said at least two detachably secured brace body segments to retain said body brace at the desired level of tightening.

22. A thoracic lumbar sacral orthosis according to claim 21, wherein said body brace is removably and adjustably secured to said front piece and said rear piece.

23. A thoracic lumbar sacral orthosis according to claim 22, wherein outer surfaces of said front piece and said rear piece include portions of hook-and-loop material complementary to portions of hook-and-loop material on at least a portion of an inner surface of said brace body.

24. A thoracic lumbar sacral orthosis according to claim 21, wherein said at least two brace body segments comprise at least three segments, said at least two sets of pulleys comprise two sets of pulleys and said at least one cable comprises two cables.

25. A thoracic lumbar sacral orthosis according to claim 24, wherein said at least three segments comprises at least one central segment having first and second opposed lateral edges, at least one first lateral segment disposed at said first opposed lateral edge of said at least one central segment and at least one second lateral segment disposed at said second opposed lateral edge.

26. A thoracic lumbar sacral orthosis according to claim 25, wherein said two sets of pulleys are disposed horizontally with respect to each other and includes a first set of pulleys mounted on said at least one central segment and said at least one first lateral segment, and a second set of pulleys is mounted on said at least one central segment and said at least one second lateral segment.

27. A thoracic lumbar sacral orthosis according to claim 25, wherein each free edge of said at least one first opposed lateral segment and said at least one second opposed lateral segment has a grasping element attached thereto.

28. A thoracic lumbar sacral orthosis according to claim 24, wherein each cable is operatively associated with a separate set of pulleys.

29. A thoracic lumbar sacral orthosis according to claim 28, wherein each set of pulleys with an associated cable provides a mechanical advantage of about 4:1 to about 30:1.

30. A thoracic lumbar sacral orthosis according to claim 21, wherein each handle element has mounted thereto a portion of a hook-and-loop material complementary to a portion of a hook-and-loop material disposed on a surface of said at least two segments.

31. A thoracic lumbar sacral orthosis according to claim 30, wherein said handle element is formed from a flexible material.

32. A thoracic lumbar sacral orthosis according to claim 21, wherein said at least two brace body segments comprise two segments, said at least one set of pulleys comprise two sets of pulleys and said at least one cable comprises two cables.

33. A thoracic lumbar sacral orthosis according to claim 21, wherein said sternal notch piece includes an adjustment piece and said front piece includes an adjustment piece receiving portion provided with an adjustable member for engaging said adjustment piece.

34. An orthotic device, comprising:
an orthosis body having two individual segments sized to wrap substantially around a torso of a wearer, each one of the two individual segments having a free end portion for positioning in front of the wearer's torso with respective ones of the free end portions adapted for releasable connection with one another and a rear portion for positioning in back of the wearer's torso;
at least one set of pulleys, each set of pulleys including two banks of pulleys with a respective one of the two banks of pulleys mounted to a respective rear portion of the orthosis body;
at least one cable for each set of pulleys, the at least one cable operatively connected to and between the two banks of pulleys and having a pair of cable free end portions and an intermediate cable portion interconnecting the pair of cable free end portions and running through at least one pulley on each of the two banks of pulleys in alteration; and
at least one handle element connected to the at least one cable at the pair of cable free end portions wherein, after the free end portions of the individual segments are releasably connected together, the wearer pulls the handle element a selected distance thereby pulling the at least one cable causing the rear portions of the orthosis body to move toward each other to tighten the orthotic device about the wearer's torso to a level of tightening desired by the wearer, the at least one handle element operative for releasable fastening on either one of the releasably connected individual segments to retain the orthotic device at the desired level of tightening.

35. An orthotic device according to claim 34, wherein the at least one handle element includes one of a hook portion of hook-and-loop fabric and loop portion of hook-and-loop fabric.

36. An orthotic device according to claim 35, wherein the at least one handle element includes a bail-shaped member connected at an end of the handle element opposite the pair of cable free end portions.

37. An orthotic device according to claim 35, wherein each one of the two individual segments includes a strip of hook-and-loop fabric extending from the free end portion towards the rear portion such that, if the at least one handle element includes the hook portion, the strip is fabricated from the loop portion and, if the at least one handle element includes the loop portion, the strip is fabricated from the hook portion.

38. An orthotic device according to claim 34, wherein at least one of the banks of pulleys is detachably connected to the individual segment.

39. An orthotic device according to claim 34, wherein the free end portions of the individual segments are detachably connected together by hook-and-loop fabric.

40. An orthotic device according to claim 34, wherein pulling the at least one cable results in a mechanical advantage dependent upon a number of pulleys mounted in each of the banks of pulleys.

41. An orthotic device, comprising:
   an orthosis body adapted to be wrapped around the torso of a wearer of the device, the orthosis body having at least two segments in juxtaposed relationship;
   means provided at free end portions of said at least two segments to releasably secure said free end portions to one another;
   at least two cables, each cable operatively connected to said at least two segments; and
   at least two sets of pulleys mounted on said at least two segments with each cable operatively connected to said at least two segments running through a pulley on each of said at least two segments in alteration, shortening of each cable pulling said at least two segments together and tightening the orthotic device with the aid of a mechanical advantage dependent upon the number of pulleys mounted on each of said at least two segments, each set of pulleys comprising two banks of pulleys and each bank of pulleys of each set of pulleys being detachably mounted on a juxtaposed edge of an adjacent segment.

42. A thoracic lumbar sacral orthosis, comprising:
   a rigid front piece;
   a sternal rear piece, removably and adjustably secured to said rigid front piece; and
   a body brace comprising:
      a brace body adapted to be wrapped around a torso of a patient, said front piece and said rear piece, said brace body comprising at least two brace body segments;
      means provided at free end portions of said at least two brace body segments for detachably securing the two free end portions together around the patient's torso;
      at least one cable operatively connected to said at least two brace body segments; and
      at least one set of pulleys mounted on each of said at least two brace segments with the cable running through a pulley on each segment in alteration, shortening of the cable pulling the at least two brace body segments together and tightening the body brace with the aid of a mechanical advantage dependent upon the number of pulleys mounted on each of said at least two brace body segments, the at least one set of pulleys comprising two banks of pulleys and each bank of pulleys being detachably mounted on a juxtaposed edge of an adjacent segment.

* * * * *

(12) EX PARTE REEXAMINATION CERTIFICATE (8775th)
United States Patent
Heinz et al.

(10) Number: US 6,213,968 C1
(45) Certificate Issued: Dec. 27, 2011

(54) CUSTOM FITTED ORTHOTIC DEVICE

(75) Inventors: Thomas J. Heinz, Flintridge, CA (US); Dae Shik Park, Fullerton, CA (US)

(73) Assignee: Bio Cybernetics International, Irvine, CA (US)

Reexamination Request:
No. 90/010,605, Jul. 17, 2009

Reexamination Certificate for:
Patent No.: 6,213,968
Issued: Apr. 10, 2001
Appl. No.: 09/334,649
Filed: Jun. 17, 1999

Related U.S. Application Data

(60) Provisional application No. 60/089,707, filed on Jun. 18, 1998.

(51) Int. Cl.
*A61F 5/02* (2006.01)

(52) U.S. Cl. .......................................... 602/19
(58) Field of Classification Search .................. None
See application file for complete search history.

(56) References Cited

To view the complete listing of prior art documents cited during the proceeding for Reexamination Control Number 90/010,605, please refer to the USPTO's public Patent Application Information Retrieval (PAIR) system under the Display References tab.

*Primary Examiner* — David O Reip

(57) ABSTRACT

An orthotic device is provided, including an orthosis body adapted to be wrapped around the torso of a wearer of the device, the orthosis body having at least two segments in juxtaposed relationship. Means are provided at free end portions of the at least two segments to releasably secure the free end portions to one another. At least two cables are provided, each cable operatively connected to the at least two segments. At least two sets of pulleys are mounted on the at least two segments with each cable operatively connected to the at least two segments running through a pulley on each of the at least two segments in alteration, shortening of each cable pulling the at least two segments together and tightening the orthotic device with the aid of a mechanical advantage dependent upon the number of pulleys mounted on each of the at least two segments.

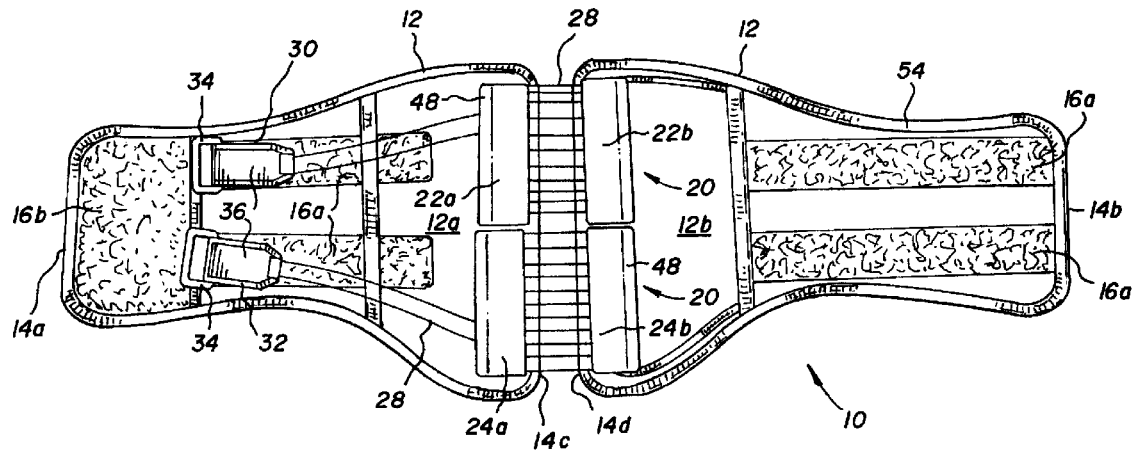

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 21, 41 and 42 is confirmed.

Claims 1 and 34 are cancelled.

New claims 43-48 are added and determined to be patentable.

Claims 2-20, 22-33 and 35-40 were not reexamined.

*43. The orthotic device of claim 1, wherein:*
*each set of pulleys comprises two banks of pulleys; and*
*each bank of pulleys of a set of pulleys is detachably mounted on a juxtaposed edge of an adjacent segment.*

*44. The orthotic device of claim 34, wherein each bank of pulleys of each set of pulleys is detachably mounted to a respective rear portion of the orthosis body.*

*45. The orthotic device of claim 1, wherein:*
*each of the at least two cables has a pair of cable free end portions; and*
*each of the at least two handle elements is connected to one of the at least two cables at only one of the pair of cable free end portions.*

*46. The orthotic device of claim 45, wherein the other one of the pair of cable free end portions is anchored to one of the at least two segments.*

*47. The orthotic device of claim 1, wherein:*
*each of the at least two cables has a pair of cable free end portions; and*
*each of the at least two handle elements is connected to one of the at least two cables at and only at the pair of cable free end portions.*

*48. The orthotic device of claim 34, wherein the at least one handle element is connected to the at least one cable only at the pair of cable free end portions.*

\* \* \* \* \*